United States Patent [19]

Alexander et al.

[11] Patent Number: 4,511,740
[45] Date of Patent: Apr. 16, 1985

[54] PROCESS FOR HYDROFORMYLATION OF TERMINAL OLEFINS TO PREDOMINANTLY LINEAR ALDEHYDES

[75] Inventors: David C. Alexander; John F. Knifton, both of Austin, Tex.

[73] Assignee: Texaco Inc., White Plains, N.Y.

[21] Appl. No.: 528,696

[22] Filed: Sep. 1, 1983

[51] Int. Cl.$^3$ ............................................. C07C 45/50
[52] U.S. Cl. ..................................... 568/454; 568/909
[58] Field of Search ................................. 568/454, 909

[56] References Cited

U.S. PATENT DOCUMENTS

| 3,239,566 | 3/1966 | Slaugh et al. | 568/454 |
| 3,239,569 | 3/1966 | Slaugh et al. | 568/454 |
| 3,641,076 | 2/1972 | Booth | 568/454 |
| 3,824,221 | 7/1974 | Ragg | 568/454 X |
| 3,847,997 | 11/1974 | Allen | 568/454 |
| 4,045,493 | 8/1977 | Trevillyan | 568/454 |
| 4,179,403 | 12/1979 | Kim | 568/454 |
| 4,198,352 | 4/1980 | Kim | 568/454 |
| 4,198,353 | 4/1980 | Carluck | 568/454 |
| 4,306,084 | 12/1981 | Pettit | 568/454 |
| 4,306,085 | 12/1981 | Kim | 568/454 |
| 4,328,125 | 5/1982 | Drago | 252/426 |
| 4,469,895 | 9/1984 | Knifton et al. | 568/454 |

FOREIGN PATENT DOCUMENTS 751353  6/1970  Belgium ............................. 568/454

OTHER PUBLICATIONS

Capha et al., "Tetrahedron Letters No. 50, pp. 4787–4790 (1971), Pergamon Press, Great Britain.
Pittman, "J. Org. Chem." vol. 46, pp. 1901–1905 (1981).

Primary Examiner—Werren B. Lone
Attorney, Agent, or Firm—Jack H. Park; Kenneth R. Priem; Cynthia L. Kendrick

[57] ABSTRACT

This invention concerns a process of preparing predominantly linear aldehydes which comprises the steps of contacting a mixture of terminal olefins and synthesis gas with a catalyst system comprising an insoluble polymeric phosphonium salt, and a ruthenium-containing compound, optionally with a cobalt carbonyl and heating said resultant reaction mixture under a pressure of 200 psi or greater at a temperature of at least 100° C. for a sufficient time to produce said aldehydes. Some of the product aldehydes will be reduced to alcohols.

17 Claims, No Drawings

PROCESS FOR HYDROFORMYLATION OF TERMINAL OLEFINS TO PREDOMINANTLY LINEAR ALDEHYDES

FIELD OF THE INVENTION

This invention concerns an improved process for preparing linear aldehydes, some of which are reduced to alcohols, by the reaction of synthesis gas and terminal olefins in the presence of a novel catalyst system.

BACKGROUND OF THE INVENTION

The processes of hydroformylation and carbonylation are well known in the art and involve reactions represented by:

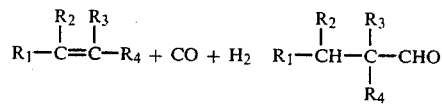

and/or

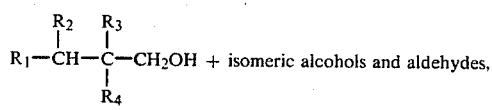

wherein the aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with consequent variation in the products obtained.

The hydroformylation reaction does not generally proceed in the absence of catalysts, and a disadvantage of many of the hydroformylation processes disclosed heretofore is their dependence upon the use of soluble cobalt or rhodium-containing catalysts, particularly the commonly-used cobalt-derived homogenous 'oxo' catalysts, which generally necessitate the use of exceedingly high pressures to remain stable under the conditions employed.

The production of aliphatic aldehyde and alcohol hydroformylation products having a relatively high normal to branched product isomer ratio and more than four carbon atoms per molecule is often difficult in many of the practical scale processes now in use. Another problem in many commonly practiced hydroformylation processes is by-product formation resulting from competing reactions. Examples of such unwanted by-products include alkanes, formed through competing olefin hydrogenation, olefin isomers formed through double bond isomerization, ketone formation and aldols generated as a result of product aldehyde condensation reactions.

In commercially practiced hydroformylation processes cobalt- and rhodium-catalyzed systems are most commonly used,[1] and while cobalt and rhodium have been the focus of much of the prior hydroformylation research, numerous other metals have been disclosed as catalysts for this synthesis.

[1](For a review of the prior art pertaining to the use of cobalt and rhodium-based hydroformylation processes see: R. L. Pruett, "Advances in Organometallic Chemistry", Vol. 17, p. 1 (1979) ).

Typical of the prior art relating to the use of ruthenium as a hydroformylation catalyst are the publications of Wilkinson and co-workers. In British Pat. No. 1,138,601, Example 6, the hydroformylation of alpha-olefins (1-hexene) to aldehydes is described using soluble, phosphine-stabilized ruthenium catalyst precursors, such as $[(Ph_2EtP)_6Ru_2Cl_2]Cl$. Here moderately high pressures are used and the use of a two step hydroformylation and subsequent hydrogenation step as a synthetic route to alcohols is discussed. Additional information regarding the use of a variety of tertiary-phosphine-ruthenium complexes in the catalytic hydroformylation of alkenes to aldehydes, particularly the dependence of conversion and aldehyde ratios upon catalyst concentration, temperature, partial and total pressures, nature of the substrate, and the addition of excess phosphine, may be found in a second publication by this group in J. Chem. Soc. p. 399 (1976). Similar classes of catalysts are disclosed also in U.S. Pat. No. 3,239,566, assigned to Shell Oil Company. In particular, this patent relates to the production of aldehydes and/or alcohols by the addition of carbon monoxide and hydrogen to olefinic hydrocarbons in the presence of a catalyst consisting of a ruthenium or rhodium component in complex combination with carbon monoxide and a trialkylphosphine. Here, the greatest percentage of the converted olefins form alcohols and aldehydes with less than seven carbons.

The use of ruthenium salts, such as ruthenium(III) chloride and ruthenium stearate, as well as ruthenium carbonyls and ruthenium-on-carbon, as catalyst precursors for the hydroformylation of olefins to straight-chain and branched aldehydes is disclosed in British Pat. Nos. 966,461 and 999,461, assigned to Imperial Industries Limited. Pettit, in U.S. Pat. No. 4,306,084, describes an oxo process reaction where the ruthenium carbonyl catalyst is maintained in a basic solution. Recently the cluster anion, $[HRu_3(CO)_{11}]^-$, has been shown to catalyze the hydroformylation of ethylene and propylene to $C_3$–$C_4$ aldehydes in dimethylformamide at 100° C. (See C. Suss-Fink, J. Organomet Chem., 193, C20 (1980)).

Polymer-bound ruthenium hydroformylation catalysts, prepared, for example, by reacting diphenylphosphinated styrenedivinylbenzene resins with ruthenium-phosphine complexes, have also been described recently. Pittman, in J. Org. Chem. 46, 1901 1981, finds improved normal/branched aldehyde ratios with these resins compared with homogeneous catalyst versions. Formation of these polymeric catalysts results from displacement of monomeric ligands from ruthenium complexes by polymeric ligands.

U.S. Pat. No. 3,239,569 discloses the production of aldehydes and alcohols in a single stage conversion which comprises contacting an olefinic hydrocarbon with carbon monoxide and hydrogen in the presence of a catalyst system comprising cobalt in complex combination with carbon monoxide and a trialkylphosphine. Here the majority of the hydroformylation products were six carbons or less.

U.S. Pat. No. 3,847,997 discloses a hydroformylation catalyst comprising a solid polymer of a tri-valent phosphorus-containing compound having associated therewith a metal from the group consisting of cobalt, rhodium, ruthenium, platinum and palladium. In the Examples recorded, the greatest weight ratio of linear aldehydes was 67 and in most examples the figure was much lower.

U.S. Pat. No. 4,045,493 describes a process for production of aldehydes and alcohols wherein a hetergeneous catalyst is employed which consists of polyphenylene comprising benzene ring structurally bonded into a polymer chain. Here, catalyst separation and recovery problems are reduced, but the percentage of straight chain products is only about 38%.

The hydroformylation catalysts discussed in U.S. Pat. No. 4,179,403 comprise an ion exchange resin, an organic linking compound ionically bound to said resin and a metal complexible moiety. The preparation of these polymeric catalysts requires the use of compounds which have both basic (or acidic) sites and transition metal ligating sites; such compounds are relatively difficult to prepare and expensive.

In another example of the use of hydroformylation catalysts comprising a metal center bonded to a polymeric ligand, U.S. Pat. No. 4,198,353 teaches of a recoverable and reusable hydroformylation catalyst having the general structure $P-MCl_3$ wherein P is a heterocyclic nitrogen-containing polymer and M is rhodium or iridium. This system overcomes the rhodium recovery problem by chemically bonding the rhodium and iridium to an insoluble polymeric pyridine support allowing recovery from the reaction mixture by direct filtration. While this invention represents an advance in catalyst recovery, there is still not a consistent high rate of conversion to straight chain aldehydes.

In U.S. Pat. No. 4,328,125 is disclosed the use of polymeric quaternary ammonium salts to prepare ionically supported transition metal catalysts. Such ammonium salts are less thermally stable than phosphonium salts, and these catalysts were prepared from relatively expensive metal complexes.

The object of this invention is to devise a ruthenium-containing hydroformylation catalyst that also contains a polymeric, phosphonium-containing counterion component, which is active for the selective oxonation of olefin substrates to their corresponding aldehydes and alcohols, and which furthermore leaves no metal in solution, thus allowing easy separation of liquid products from the insoluble polymeric catalyst. Additionally an object is to produce predominantly linear aldehydes. A further object is to devise a system which shows reasonable activity at low pressures.

It should be noted that in previously disclosed polymeric hydroformylation catalysts polymeric electronically neutral ligands have generally been used as supports; in these the metal center is coordinated to the support through dative bonding (FIG. 1A). With the catalyst of this invention a polymeric phosphonium cation serves as support, which results in the formation of a transition metal complex ionically bonded to the support. (FIG. 1B). Furthermore, the use of this invention of readily available ruthenium-containing catalyst precursors such as ruthenium (IV) oxide instead of more expensive complexes is advantageous.

FIG. 1

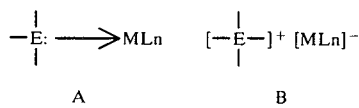

WHERE: E = PHOSPHORUS OR NITROGEN,
M = METAL AND L-ONE OR MORE LIGANDS.

SUMMARY OF THE INVENTION

This invention concerns a method of producing linear aldehydes which comprises the steps of contacting a mixture of CO and $H_2$ and a terminal olefin with a catalyst system comprising an insoluble polymeric phosphonium salt and a ruthenium-containing compound, optionally with a cobalt carbonyl, heating said reaction mixture under a pressure of 200 psi or greater at a temperature of at least 100° C. for a sufficient time to produce said aldehydes, some of which will be reduced to alcohols, and isolating said linear aldehydes.

DETAILED DESCRIPTION OF THE INVENTION

In the narrower and more preferred practice of this invention, normal aldehydes are prepared from a synthesis gas mixture of carbon monoxide, hydrogen and terminal olefin substrates by a process comprising the following steps:

(a) Contacting said mixture of carbon monoxide, hydrogen and a terminal olefin with a catalyst system comprising an insoluble polymeric phosphonium salt, a ruthenium-containing compound and optionally a cobalt carbonyl compound, (b) Heating said reaction mixture to a temperature of at least 100° C., at a pressure of 200 psi or greater, and (c) Isolating said normal aldehydes contained therein, some of which will be reduced to alcohols.

In order to present the inventive concept in the greatest possible detail to promote its understanding, the following supplementary disclosure is submitted. The basic invention, improved upon here, is practiced as follows:

Catalysts which are suitable in the practice of this invention contain ruthenium. The ruthenium-containing catalyst may be chosen from a wide variety of organic or inorganic compounds, complexes, etc. It is only necessary that the catalyst precursor actually employed contain said metal in any of its ionic states. The actual catalytically active species is then believed to comprise ruthenium in complex combination with carbon monoxide, hydrogen, polymeric phosphonium salts and optionally cobalt. The most effective catalyst is believed to be achieved where ruthenium oxides and cobalt carbonyls are mixed with an insoluble polymeric phosphonium salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide.

Preferred ruthenium-containing compounds are oxides of ruthenium. Among the particularly preferred is ruthenium(IV) dioxide hydrate ($RuO_2 \times H_2O$). The usefulness of these ruthenium compounds for aldehyde synthesis is illustrated by the accompanying Examples.

The ruthenium-containing compound is, prior to its catalytic use in making aldehydes, first mixed with an insoluble polymeric phosphonium salt.

In the novel catalyst system of this invention for forming linear aldehydes, an insoluble polymeric phosphonium salt is mixed with a ruthenium oxide compound which serves to promote the reaction of olefinic materials with carbon monoxide and hydrogen. In the absence of the polymeric phosphonium salt (i.e. with only $RuO_2$ and optionally $Co_2(CO)_8$ in 1 octene), selectivity to linear products is lower, and reduction to alcohols occurs to a greater extent.

Any insoluble polymer phosphonium salt is suitable for the practice of this invention. The phosphonium group may be bonded directly to the polymer backbone, it may be bonded to the polymer through a series of alkylene groupings or it may be incorporated into the polymer backbone.

The insoluble polymeric phosphonium salt employed in the catalyst system of this invention preferably contains polymers of phosphonium salts having the formula:

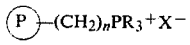

wherein

ⓟ— an insoluble polymeric framework selected from the group of polymers that includes polystyrene crosslinked with divinylbenzene, polyethylene and polymethacrylamide.

R is one or more alkyl or aryl radicals each containing one to twenty carbon atoms;

X is halogen or an acetate grouping; and n is 0→3.

Examples of suitable insoluble polymeric phosphonium salts include poly(methacrylamidopropyltributylphosphonium chloride), polyvinyltributylphosphonium chloride, and polystyrylmethyltributylphosphonium chloride. The most preferred polymeric phosphonium salt is polystyrylmethyltributylphosphonium chloride.

The polystyrylmethyltributylphosphonium chlorides were prepared as described in J. Am Chem. Soc. 1979, 101, 3920-3827 by Molinari and coworkers. The phosphonium content ranged from 0.5 to 2.0 meg/g.

The physical appearance of the polymeric phosphonium salt is generally a white powder. After contact with $RuO_2$ and $Co_2(CO)_8$ under the reaction conditions it becomes green in color and can be filtered in air, washed with solvent and reused without the addition of more metal compounds. The hydroformylation activity of the green polymer is retained without significant decrease through four or more cycles.

The addition of the polymeric phosphonium salt to the ruthenium-containing compounds described supra promotes the following improvements in olefin hydroformylation performance:

(1) Improved yields of desired aldehydes.
(2) Higher selectivity to linear aldehyde products.
(3) Less by-product hydrocarbon formation.
(4) Ease of separation of the ruthenium catalyst from the aldehyde and alcohol products.
(5) Ability to reuse the polymer with only minor loss of activity.

Illustrative of these improvements are the accompanying examples, particularly Examples IX-XI and comparative Example XII, as well as the ruthenium catalyst recycle experiments of Examples II-IV.

In the absence of the polymeric phosphonium salt (i.e. with only $RuO_2$ and $Co_2(CO)_8$ in 1-octene) the hydroformylation rate is higher, but selectivity to linear products is much lower, and reduction to alcohols occurs to a greater extent.

Polymeric ammonium salts are ineffective because of their reduced thermal stability and because they are not suitable counterions for the active catalyst, giving more highly colored solutions.

A cobalt-containing compound is optional in the process of this invention. Use of dicobalt octacarbonyl, $Co_2(CO)_8$, alone with the polymeric phosphonium salt results in essentially no conversion under these conditions. However, use of $RuO_2$ alone with the polymeric phosphonium salt gives an orange polymer of lesser utility on reuse because of declining reactivity and selectivity.

The cobalt-containing compound which may optionally be used in the catalyst composition may take different forms. For instance, the cobalt may be added to the reaction mixture in the form of a carbonyl derivative. Examples of these include, among others, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_{18}$ and derivatives thereof by reaction with ligands, and preferably group V donors of the group including phosphines, arsines and stibine derivatives of the formula $(Co(CO)_3L)_2$ wherein L is $PR_3$, $AsR_3$ and $SbR_3$ wherein R is a hydrocarbon radical, with further examples including cobalt carbonyl hydrides, cobalt carbonyl halides, cobalt nitrosyl carbonyls, represented by $CoNO(CO)_3$, $Co(NO)(CO)_2PPh_3$, and organometallic compounds obtained by reacting cobalt carbonyls with olefins, allyl and acetylene compounds, of the group including bis(-cyclopentandienyl) cobalt, $(C_5H_5)_2Co$, cyclopentadienyl cobalt dicarbonyl and bis(hexamethyl-benzene)cobalt.

Preferred cobalt-containing compounds to be used in the catalyst system comprise those having at least one cobalt atom attached to carbon, of the group including cobalt carbonyls and their derivatives, represented by dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt discarbonyl, cobalt carbonyl halides, and the like, and mixtures thereof.

Particularly preferred cobalt-containing compounds to be used in the catalyst comprise those having at least one cobalt atom attached to at least three separate carbon atoms, as represented by the dicobalt octacarbonyls and their derivatives.

The olefins employed in the practice of this invention include terminal olefins containing two to twenty carbon atoms and mixtures of the same. Examples of suitable olefins include straight-chain terminal olefins such as propylene, 1-butene, 1-octene, 1-decene, 1-dodecene, 1-tetradecene, and 1-hexadecene. Also suitable are branched-chain, terminal olefins such as 3-methyl-1-pentene, 4-methyl-1-hexene, 3,3-dimethyl-1-butene and 3,4-dimethyl-1-hexene.

Particularly preferred are straight-chain terminal olefins represented by propylene, 1-butene, 1-octene, 1-decene and 1-dodecene.

A solvent or liquid diluent is not necessary in the process of this invention, although they may be used. A wide variety of solvents or diluents may be used, including hydrocarbon and oxygenated hydrocarbons. Suitable oxygenated hydrocarbon solvents are compounds composed only of carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms.

Preferred ester type solvents are the aliphatic and acyclic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents are, for example, cyclic ketones including cyclohexanone, 2-methylcyclohexanone, as well as acylic ketones including 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers, including 1,4-dioxane or p-dioxane, etc. Hydrocarbon solvents, such as hexane, heptane, decane, dodecane, tetradecane, etc. are also suitable solvents for use in this invention.

In the practice of this invention, it is also possible to add a small amount of water to the solvent or diluent and still obtain satisfactory results.

The quantity of ruthenium catalyst (exclusive of polymeric salt) employed in the instant invention is not critical and may vary over a wide range. In general, the novel process is desirably conducted in the presence of a catalytically effective quantity of the active ruthenium species and insoluble polymeric phosphonium salt which gives the desired products in reasonable yields. The reaction proceeds when employing as little as about $1 \times 10^{-6}$ weight percent, and even lesser amounts, of ruthenium together with about one weight percent of polymeric phosphonium salt, basis the total weight of the reaction mixture. The upper concentration is dictated by a variety of factors including catalyst cost, partial pressures of carbon monoxide and hydrogen, operating temperature etc. A ruthenium catalyst concentration of from about $1 \times 10^{-5}$ to about 30 weight percent ruthenium in conjunction with an insoluble polymeric phosphonium salt concentration of from about 2 to about 50 weight percent, based on the total weight of reaction mixture is generally desirable in the practice of this invention. The preferred ruthenium to insoluble polymeric phosphonium salt atomic ratio is about 0.01 to 1.0.

The temperature range which can usefully be employed in these syntheses is a variable dependent upon other experimental factors, including the pressure, the concentration and the choice of the particular species of ruthenium catalyst among other things. The range of operability is from about 100° to 200° C. when superatmospheric pressures of syngas are employed. A narrow range of 120°–150° C. represents the preferred temperature range.

Superatmospheric pressure of 200 psi or greater lead to substantial yields of alcohols and aldehydes by the process of this invention. A preferred operating range is above 500 psi. The most preferred range is from 600–800 psi, but pressures of as much as 7000 psi or more are useful.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases of the group including nitrogen, argon, neon and the like, or they may include gases that may or may not undergo reaction under CO hydrogenation conditions, as represented by carbon dioxide, hydrocarbons including methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The major by-products of these aldehyde syntheses are commonly alkanes, isomerized olefins, and aldols, formed both through condensations with the product aldehydes, and in some cases, from subsequent dehydration and reduction of the initially formed aldol. Some of the aldehydes produced are immediately reduced to alcohols.

The aldehyde and alcohol products may be readily separated from the polymeric catalyst by simple filtration. The by-products identified supra may also be isolated by conventional means, or they may be recycled with the ruthenium catalysts.

The novel process of this invention can be conducted in a batch, semi-continuous or continuous fashion. The polymeric catalyst is well suited for use in a continuous tubular reactor, or it may be employed in a series of batch reactions with catalyst isolation by filtration or decantation after each cycle. Operating conditions can be adjusted to optimize the formation of the desired alcohol product, and said material may be recovered by methods well known in the art, such as distillation, fractionation, extraction and the like.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. All temperatures are in degrees centigrade and all pressures are in pounds per square inch gauge (psig).

Having described the inventive process, the following examples are submitted to supply specific and illustrative embodiments.

EXAMPLE I

In this example 1-octene (17.9 g, 159 mmole), polystyrylmethyltributylphosphonium chloride (1.2 g, ca. 2.5 mmole phosphonium chloride), dicobalt octacarbonyl (0.030 g, 0.09 mmole), and ruthenium(IV) oxide hydrate (0.035 g, 0.019 mmol) are charged to a 300 ml stainless steel autoclave, which is then sealed, flushed with CO/$H_2$ (½), and pressurized to 600 psi CO/$H_2$ (½). The reaction mixture is then heated to 150° C. with stirring and held at temperature for 16 hours. After the reactor is cooled and vented the products are recovered as a green polymer and a clear, colorless liquid. Analysis of the organic products is by gas-liquid chromatography. The following composition for the liquid product was obtained:

| | |
|---|---|
| Octane | 6.04% |
| Octene | 66.9% |
| $C_9$ aldehydes | 21.7% |

| C9 alcohols | 3.79% |

Linearity of the aldehydes was 67%.

Reaction solutions typically contained no detectable cobalt and 20–45 ppm ruthenium.

EXAMPLES II–IV

Example II–IV were conducted using the same ruthenium-cobalt polystyrylmethyltributylphosphonium chloride catalyst and hydroformylation conditions as Example I. After olefin oxonation, the polymeric catalyst was isolated from the product aldehyde and unreacted 1-octene by filtration, washed with solvents, and reused for successive olefin hydroformylations. Recycle of the same Ru-Co-polymer catalyst led to only a minor loss of activity. The lower conversions in the series of Examples II–IV result primarily from not using the entire sample for successive reactions. Analysis of the resulting crude liquid product showed the following:

TABLE I

| | Product Composition (%) | | | | Aldehyde | | Mmol prod/ |
| | Octane | Octene | $C_9$ Aldehydes | $C_9$ Alcohols | Linearity (%) | Ru/Co | mg-atom metal |
| --- | --- | --- | --- | --- | --- | --- | --- |
| Example II | 6.6 | 54.3 | 31.6 | 4.5 | 78 | 1 | 172 |
| III | 4.8 | 66.6 | 24.5 | 2.8 | 75 | 1 | 170 |
| IV | 4.3 | 77.6 | 15.8 | 1.4 | 73 | 1 | 163 |

EXAMPLES V–VIII

Examples V–VIII were conducted the same manner as Example I, except the ratio of Ru/Co was reduced in each Example.

The Ru/Co ratios were 0.5, 0.2, 0.1 and 0 respectively. Analysis of the resulting product of each example is shown in the following Table II:

TABLE II

| | Product Composition (%) | | | | Aldehyde | Mmol prod/ |
| | Octane | Octene | $C_9$ Aldehydes | $C_9$ Alcohols | Linearity (%) | mg-atom metal |
| --- | --- | --- | --- | --- | --- | --- |
| Example V | 5.1 | 70.0 | 19.5 | 4.0 | 67 | 150 |
| VI | 5.8 | 82.8 | 9.8 | 2.5 | 61 | 92 |
| VII | 3.1 | 92.5 | 2.1 | 1.0 | — | 32 |
| VIII | — | — | <1 | — | — | — |

EXAMPLES IX–XI

Examples IX–XI show results of reactions carried out in the absence of cobalt carbonyl using as a catalyst a ruthenium component and an insoluble polymeric phosphonium salt component. The reactions of all three Examples were carried out at 125° C. with 600–800 psi of 1/1 CO/$H_2$ and 17.9 g of 1-octene. In Example IX 1.1 g of polymeric phosphonium salt and 0.138 g $RuO_2$ were charged, and the orange polymer isolated by filtration after the reaction was used as catalyst in Example X. This procedure was repeated for Example XI. Analysis of the resulting product of each example is shown on the following Table III:

TABLE III

| | Product Composition (%) | | | | Aldehyde Linearity (%) |
| | Octane | Octene | $C_9$ Aldehydes | $C_9$ Alcohols | |
| --- | --- | --- | --- | --- | --- |
| Example IX | 5.4 | 75.3 | 17.9 | — | 76 |
| X | 4.4 | 74.1 | 19.8 | 0.6 | 84 |
| XI | 5.3 | 75.9 | 8.6 | 2.3 | 78 |

COMPARATIVE EXAMPLE XII

Example XII was conducted the same as Example I, except no polystyrylmethyltributylphosphonium chloride was added to the mixture. Analysis of the crude product liquid showed the composition to be:

| Octane | 7.5% |
| Octene | 0.9% |
| $C_9$ Aldehydes | 33.8% |
| $C_9$ Alcohols | 36.6% |
| Aldehyde Linearity | 31% |
| Mmole of Product/Mg atom - metal | 450 |

EXAMPLE XIII

In Example XIII internal octenes were charged in the olefin mixture instead of terminal octenes in order to demonstrate the reduced reactivity of internal octenes. Analysis of the crude liquid product showed the following:

| Octane | 3.1% |
| Octene | 92.5% |
| $C_9$ Aldehydes | 2.4% |
| $C_9$ Alcohols | 0.3% |

EXAMPLE XIV–XV

Table IV lists the results of Examples XIV and XV which were conducted the same as Example I with the exception of temperature. In Example XIV the temperature used was 160° C. and in Example XV it was 125° C. The following data gives an indication of the effects of various temperatures. Higher temperatures lead to increased amounts of alcohols, higher conversions, and reduced selectivity to linear aldehydes.

TABLE IV

|  | | Product Composition (%) | | | Aldehyde Linearity (%) |
|---|---|---|---|---|---|
|  |  | Octane | Octene | C$_9$ Aldehydes | C$_9$ Alcohols | |
| Exam- | XIV | 9.7 | 50.0 | 19.7 | 13.9 | 53 |
| ple | XV | 2.3 | 85.3 | 11.3 | — | 68 |

EXAMPLE XVI

As discussed, a solvent or diluent is not necessary for the process of this invention, but one can be used. Example XVI illustrates the use of the solvent p-dioxane. The typical procedure of Example I was followed except 10 ml of 1-octene and 20 ml of dioxane were used. The crude liquid product shows the following compositions:

| | |
|---|---|
| Solvent | 66.5% |
| Octane | 2.5% |
| Octene | 13.0% |
| C$_9$ Aldehydes | 10.3% |
| C$_9$ Alcohols | 2.7% |
| Aldehyde Linearity | 71.0% |

What is claimed is:

1. A process for preparing predominantly linear aldehydes containing from 3 to 21 carbon atoms which comprises the steps of
contacting straight chain terminal olefins, with 2 to 20 carbons, carbon monoxide and hydrogen with a catalyst system comprising a ruthenium-containing compound and optionally a cobalt-containing compound mixed with an insoluble polymeric phosphonium salt of the formula:

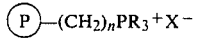$-(CH_2)_n PR_3^+ X^-$ where (P) is an insoluble polymeric framework selected from the group of polymers consisting of polystyrene crosslinked with divinylbenzene, polyethylene and polymethyacrylamide, R is one or more alkyl or aryl radicals each containing one to twenty carbon atoms, x is halogen or an acetate grouping, n is 0→3, heating resultant reaction mixture under a pressure of 200 psi or greater at a temperature of at least 100° C. and isolating said linear aldehydes.

2. The process of claim 1 wherein the ruthenium-containing compound is selected from the group consisting of one or more oxides of ruthenium.

3. The process of claim 2 wherein the oxide of ruthenium is selected from the group consisting of anhydrous ruthenium(IV) dioxide, ruthenium(IV) dioxide hydrate, and ruthenium(VIII) tetraoxide.

4. The process of claim 3 wherein said ruthenium oxide compound is ruthenium(IV) oxide.

5. The process of claim 1 wherein R is a butyl radical and x is chloride.

6. The process of claim 1 wherein the insoluble polymeric phosphonium salt is selected from the group consisting of polymethacrylamidopropyltributylphosphonium chloride, polyvinyltributylphosphonium chloride and polystyrylmethyltributylphosphonium chloride.

7. The process of claim 1 wherein the preferred insoluble polymeric phosphonium salt is polystyrylmethyltributylphosphonium chloride.

8. The process of claim 1 wherein the cobalt compound is selected from cobalt carbonyls of the group consisting of dicobalt octacarbonyl, tetracobalt dodecacarbonyl, hexacobalt hexadecacarbonyl and derivatives thereof by reaction with ligands and preferably group V donors of the group of phosphines, arsines and stibine derivatives of the formula (Co(CO)$_3$L)$_2$ wherein L is PR$_3$, AsR$_3$ and SbR$_3$ wherein R is a hydrocarbon radical, cobalt carbonyl hydride, cobalt carbonyl halide, cobalt nitrosyl carbonyl and organometallic compounds obtained by reacting cobalt carbonyls with olefin, allyl and acetylene compounds.

9. The process of claim 8 wherein the preferred cobalt compound is dicobalt octacarbonyl.

10. The process of claim 1 wherein the mixture is under a pressure of 200-7000 psi.

11. The process of claim 1 wherein the mixture is under a pressure of 600-800 psi.

12. The process of claim 1 wherein the temperature is 100°-200° C.

13. The process of claim 1 wherein the temperature is 120°-150° C.

14. The process of claim 1 wherein the olefins used are terminal olefins with 2 to 20 carbons.

15. The process of claim 14 wherein the terminal olefins are selected from the group consisting of propylene, 1-octene, 1-decene, 1-dodecene, 1-hexadecene and 1-hexene.

16. The process of claim 15 wherein the terminal olefin is 1 octene.

17. The process of claim 1 wherein the synthesis gas is composed of hydrogen and carbon monoxide in a molar ratio ranging from 1:5 to 5:1.

* * * * *